(12) United States Patent
Moore

(10) Patent No.: US 7,648,834 B2
(45) Date of Patent: Jan. 19, 2010

(54) PLASMON FLUORESCENCE AUGMENTATION FOR CHEMICAL AND BIOLOGICAL TESTING APPARATUS

(76) Inventor: Wayne E. Moore, 11812 Sweetland Way, Columbia, MD (US) 21044

( * ) Notice: Subject to any disclaimer, the term of this patent is extended or adjusted under 35 U.S.C. 154(b) by 95 days.

(21) Appl. No.: 11/333,700

(22) Filed: Jan. 17, 2006

(65) Prior Publication Data

US 2007/0166761 A1 Jul. 19, 2007

(51) Int. Cl.
*C12M 1/34* (2006.01)
(52) U.S. Cl. .................................. 435/287.1
(58) Field of Classification Search ............... 436/518; 435/287.1, 4; 422/50
See application file for complete search history.

(56) References Cited

U.S. PATENT DOCUMENTS

| 5,837,552 | A | 11/1998 | Cotton et al. | |
| 5,866,433 | A | 2/1999 | Schalkhammer et al. | |
| 6,753,995 | B2 * | 6/2004 | Wang | 359/271 |
| 7,195,872 | B2 * | 3/2007 | Agrawal et al. | 435/6 |
| 2002/0167256 | A1 * | 11/2002 | Iwasaki et al. | 313/309 |

FOREIGN PATENT DOCUMENTS

EP 732583 9/1996

OTHER PUBLICATIONS

Zeman, Ellen J. et al. An accurate Electromagnet tjepru Theory . . . Journal of Physical Chemistry, 1987, 91, 634-643.
Philpott, Michael R. Effect of surface plasmons on . . . Journal of Chemical Physics, Vo. 62, No. 5, Mar. 1, 1975.
Pendry, John Playing Tricks with light. Science, vol. 285 Sep. 10, 1999 1687-1688.
Gersten, Joel I. et al. Photophysics and photochemistry . . . Surface Science 158(1985) 165-189.
Gersten, Joel Spectroscopic properties of molecule . . . et al. Journal Chemical Physics 75(3) Aug. 1, 1981, 1139-1152.
Garcie-Vidal, F. J. Silver-filled carbon nantobues . . . Physical Review B vol. 58 No. 11 Sep. 15, 1998-I, 6783-8786.
Das, Purna etal. Enhancement of molecular fluorescence . . . Journal of Physical Chemistry 1985 89 4680-4687.
Chew, H. Transition rates of atoms near spherical . . . Journal of Chemical Physics 87 (2) Jul. 15, 1987 1355-1360.
Wokaun, A. Surface enhancement of optical fields.. Molecular Physics, 1-33, 1985.
Kummerlen, J. et al. Enhanced dye fluorescence over . . . Molecular Physics 1993, Vo. 80, No. 5. 1031-1046.
Ditlbacher, H. et al. Electromagnetic interaction of . . . Applied Physics B (2001) unpaged, 5 pages.
Wenseleers, Wim et al. Five Orders-of-Magnitude . . . Journal of Physical Chemistry B 2002, 106, 6853-6863.
Weitz, D.A. et al. Fluorescent lifetimes of molecules . . . Optics Letters Feb. 1982 vol. 7 No. 2 89-91.
Tarcha, Peter J. et al. Surface-enhanced fluorescence on . . . Applied Spectroscopy vol. 53, No. 1, 1999, 43-48.
Stitch, Norbert et al. Nanofilms and nanoclusters: Energy.. Journal of Nanoscience and Nanotechnology 2001, vol. 1, No. 1, 397-405.
Sokolov, Konstantin et al. Enhancement of molecular . . . Analytical Chemistry, vol. 70, No. 18, Sep. 15, 1998, 3898-3905.
Selvan, S. Tamil et al. Remarkable Influence of silver . . . Journal of Physical Chemistry B, 1999, 103, 7064-7067.
Pugh, Vincent J. et al. Submicrometer spatial resolution . . . Applied Spectroscopy, vol. 57, No. 12, 2003, 1592-1598.
Mohammed, Mona B. et al. The'lightning' gold nanorods:.. Chemical Physics Letters 317(2000) 517-523.
Matyushin, Viatcheslav et al. Tuning the setup of sputter . . . Journal of Nanoscience and Nanotechnology 2004 vol. 4 No. 1/298-105.
Malicka, Joanna et al. Effects of fluorophore0to-silver . . . Analytical Biochemistry 315 (2003) 57-66.
Lakowicz, Joseph R. et al. Intrinsic fluorescence from . . . Biochemical and Biophysical Research Communications 286, 875-879 (2001).
Lakowicz, Joseph R. Radiative decay engineering: biophy . . . Analytical Biochemistry 298, 1-24 (2001).
Glass, A. M. et al. Interaction of metal particles with . . . Optics Letters vol. 5, No. 9, Sep. 1980, 368-370.
Geddes, Chris D. et al. Silver fractal-like structures . . . Journal of Fluorescence, vol. 13, No. 3, May 2003, 267-276.
Geddes, Chris D. et al. Fluorescence News Fractal Silver . . . Journal of Fluorescence, vol. 13, No. 2, Mar. 2003 119-122.
Aroca, R. Fluorescence enhancement from Langmuir-Blodgett . . . Langmuir 1988, 4, 518-521.
Hayakawa, Tomokatsu, Field enhancement effect of small Ag . . . Applied Physics Letters, vol. 74, No. 11, Mar. 15, 1999, 1513-1515.

* cited by examiner

*Primary Examiner*—Ann Y Lam
(74) *Attorney, Agent, or Firm*—William S. Ramsey

(57) ABSTRACT

The sensitivity and durability of fluorescent assays may be increased through structures and methods using plasmon fluorescence augmentation and sealing of the structure against degradation by reagents used in the assay. The resulting structures make practical extremely sensitive fluorescent assays for DNA and other biological analytes.

7 Claims, 8 Drawing Sheets

PLASMON FLUORESCENCE AUGMENTATION FOR CHEMICAL AND BIOLOGICAL TESTING APPARATUS

STATEMENT REGARDING FEDERALLY SPONSORED RESEARCH OR DEVELOPMENT

The work leading to this application was supported in part by the US Government under grant SBIR Phase I-NIH 1R43 CA097569-01 and DoD Contract MDA904-02-C-0701.

CROSS-REFERENCE TO RELATED APPLICATIONS

Not Applicable.

REFERENCE TO A "MICROFICHE APPENDIX"

Not Applicable.

BACKGROUND OF THE INVENTION

1. Field of the Invention

The invention pertains to manufacturing robust devices employing particle plasmon resonance to improve microarray bioassay performance.

2. Description of Related Art Including Information Disclosed Under 37 CFR 1.97 and 37 CFR 1.98

The use of metallic nanostructures to create altered spectral effects from fluorescent molecules has been known for decades. Both the fluorescent intensity and lifetime can be beneficially altered using metal nanostructures. The most relevant references, e.g., U.S. Pat. No. 5,866,433 ('433) and U.S. Pat. No. 5,837,552 ('552), both incorporated herein by reference, describe embodiments that in one manner or another place metal nanoparticles on substrates and use specific biological binding to draw fluorescent material into the vicinity of the metal nanoparticle layer.

The prior art has described a substrate, which can effectively be any supporting structure, planar or three-dimensional, upon which a layer of conductive nanoparticles are made to adhere. Nanoparticles are generally objects less than 1 micron in lateral and axial dimensions, and for applications to fluorescent enhancement are generally described as smaller than a wavelength of the "light". The reference to "light" in the prior art is often vague. Since this is a fluorescent system, there are at least two spectra to consider, the excitation and fluorescent emission spectra. Since, in general these partially overlap and have peaks fairly close to each other, the distinction between which wavelength is more important has not been clarified in the prior art. There is however, a decisive physical phenomenon that clearly dictates the size of nanoparticles for optimum enhancement, that being nanoparticle plasmon resonance.

The "size" of nanoparticles is also vague in the prior art. Size and shape are in fact both important in the enhancement mechanisms and some recent literature has begun to explore the importance of nanoparticle shape. In the conventions of the prior art, if a nanoparticle is a flat disk, the size would likely refer to its lateral dimension defined by the diameter. If the nanoparticle were rod shaped, the size might be taken as the length, however, the diameter of the rod is also important. The details of size and shape that accrue to optimized enhancement are not completely understood, so there is a necessary void in the descriptions found in prior art. Therefore the prior art provides only clues regarding the ability to reliably and repeatedly fabricate nanoparticles with predictable behaviors.

The thickness of nanoparticles, optical properties of the nanoparticle film, spatial density of the nanoparticles within the film, as well as the number of layers of nanoparticles comprising the "film" are all referred to generally in the prior art. It is taken by most references and specifically by '433 and '552 that the nanoparticles should have a thickness in the range of 2 nm to 25 nm. Nevertheless, vacuum and chemical deposition methods are capable of extremely well defined layer thickness, and the need for generality is unclear. In fact, some references teach metal islands spaced apart, or metal islands spaced apart that may be connected by thinner or different metal structures, or metal islands that may be touching. In each of these cases it can be successfully shown that an enhancing effect occurs, however, the physical mechanisms and design parameters required to provide a maximum effect are not taught. This is largely because the design of an enhancing structure is not just a nanoparticle design problem, it is a system design problem.

Another interesting factor emerges when considering the nature of nanoparticles described in the prior art. Since the very first experiments were conducted over 25 years ago using chemically deposited silver, the method of chemical deposition has been observed and repeated by others. This method does result in a layer of island-like discrete nanoparticles that, in general do not contract each other. It is also possible to obtain such "metal island" films using vacuum deposition methods such as sputtering or thermal evaporation. These films are often semi transparent to incident light since the metal film has a relatively low spatial density. These metal island films are described in all of the prior art. It has been found, however, that thin, conductive, solid films of many metals can be deposited with high adhesion and high fluorescence enhancement, however, these films are not comprised of island-like metal structures. They are instead comprised of columnar metal crystals typically expected by those skilled in the art of thin film vacuum deposition. These metal layers, usually being well over 20 nanometers thick, are characterized by a columnar nanostructure that has surfaces that "appear" to be bumpy. The bumps have the appearance of nanoparticles when viewed using an atomic force microscope (AFM) or scanning electron microscope (SEM), however, they are not discrete particles and behave electrically differently than the discrete particle films of prior art. Interestingly, if the surface features, bumps, have apparent diameters in the range of 20 to 300 nm fluorescence enhancement is observed similar to that seen with island films. The physical phenomena accounting for the coupling of electrical field energy from an exciting light field to the plasmon field of this nanostructured surface is not well defined in theory, but it is clear that the metallic structures are completely different from the island-like structures found in the prior art. Further, it is found that the conditions for optimum fluorescence enhancement are also markedly different from those required for island structures. This invention addresses enhancement mechanisms created using thin, deliberately nanostructured, continuous metal films that are not made of island-like metal nanoparticles. Therefore, there is a clear distinction between the terms nanoparticle and nanostructure as used herein. Much of the background discussion relating to the prior art of island-like nanoparticle films is nevertheless relevant. In this discussion the terminology of the prior art is used where appropriate and will be distinguished from methods of the invention using nanostructured films.

It is well recognized in the prior art that some form of preparation must be performed on the substrate supporting the enhancing metallic nanoparticles. Silanization is taught in '552, and other methods of causing metals to adhere to plastics and glasses are well known in industry. Nevertheless, the method of adhering the active metal to a substrate can interact with the operative physical mechanisms and cause the resulting enhancement to be greater or smaller. Further, in some structures, the adhesion process can be vulnerable to external chemical attack leading to definite limitations in the lifetime and practicality of a product. Similarly, metalization layers used to create adhesion, e.g., chromium, tungsten, titanium, palladium and others can alloy with the active nanoparticles and change their plasmonic properties; resonance, damping, etc. Moreover, a design that has all dimensions optimized for one set of materials will not be optimum for a different choice of materials. The prior art alludes only vaguely to the attachment methods, yet, without adhesion between the active nanoparticles and the substrate, a practical structure cannot be built. While the need for adhesion may seem obvious, the proper choice of materials and processes that results in a well adhering film with substantial enhancement is indeed not obvious and is not taught elsewhere.

The enhancement mechanism is known to be due to the mutual coupling of energy from a plasmon electrical field to the fluorophore. It is well known and taught that nanoparticle and surface plasmon energetic coupling mechanisms, like all energetic coupling mechanisms, has distance dependence. In fact, in general, it has more than one distance dependent mechanism, is highly non-linear, as has only recently been partially understood. The methods and parameters enabling the ability to design reliably working structures that make deliberate use of the distance dependencies have not been taught. As measured from the original surface of the substrate, the prior art speaks of accomplishing the required separation between the mean surface height of the metal nanoparticle layer, and the mean fluorophore location distance by using an intervening layer of material which may or may not be part of the biological assay system. Layers are called biorecognitive or coupling layers and have been exemplified as layers of tissues, polymers, or other materials. In fact, all of these are completely viable methods, as is also, for example, choosing an appropriate DNA strand length which binds a labeled DNA analyte in a manner to place the fluorescent labeling molecule an appropriate distance from the metal surface. However, the term "appropriate distance" is unclear in the prior art. The prior art does not reveal that if one defines the system of materials used in a specific enhancing structure, the optimum separation distance can be specified empirically with reliable precision leading to optimized, manufacturable and reliable structures.

It is well taught that microarray substrates are exposed to many harsh compounds, salts, acids, and bases, often at elevated temperatures. Metallic films, such as silver, are subject to corrosion. Much work through the ages has gone into finding coatings that can protect mirrors and other optical surfaces. In the case of optical instruments, the films requiring protection are generally many microns thick and are solid uniform films. In comparison, the art of nanoparticle plasmon devices requires films of nanoparticles, or nanoclusters, of metal. Working films are usually less than 50 nanometers thick and are made of tiny grains of material, all of which are particularly vulnerable to chemical attack. After hundreds of attempts by the inventors and others to fabricate a robust, chemically resistant film of silver nanoparticles, it appears that the prior art has overlooked or underestimated the difficulty of using such films in real, practical biotechnology applications. Devices built according to the descriptions available in all literature discovered by this team failed almost immediately when exposed to assay protocols. So, while the science revealed elsewhere is of great fundamental value, the practical application of nanoparticle plasmon technology to microarrays has not been previously accomplished.

It is broadly recognized throughout the entire community of microarray and microplate users, including both researchers and applied clinicians that the data quality of microarrays needs to be improved in the interest of more rapidly advancing human health. Critical needs exist in cancer research, viral research, and drug discovery for more sensitive and accurate means of discovering disease and the cures for disease. As regards the specific problems facing microarray users, few truly effective methods have been found to accomplish this illusive goal. The use of metal enhanced fluorescence has been recognized by a few to offer a potential solution. Yet, while the prior art successfully characterizes a general phenomenon and indicates a broad range of parameters for fabricating devices, the prior art fails to address most of the critical parameters with sufficient detail or accuracy to permit the fabrication of practical structures. The prior art frequently and eloquently describes bioassay principles and well known bioassay surface preparation methods, yet none describe a practical manufacturing protocol for a nanoparticle plasmon sensor embodiment that absolutely improves assay sensitivity in a commercially viable embodiment. Summarizing the prior art it is clear that a need exists for a microarray substrate comprising a material system that provides: stable material adhesion to glass and plastic substrates; high plasmon field enhancement; high coupling of enhanced plasmon energy into fluorescent molecules causing significantly enhanced fluorescence emission; and simultaneously being substantially free from corrosion in bioassay buffer solutions. The prior art has focused on the use of discrete nanoparticle films which have distinct behaviors and limitations. The improved invention of this application addresses these issues and results in a complete description of several practical and practicable embodiments of assay substrates of significant value to the life sciences.

Publications in the Technical Area.

Surface Enhanced Fluorescence: Experiments Only, No Theory, Metal Enhanced Fluorescence (MEF)

R. Aroca, G. J. Kowacs, C. A. Jennings, R. O. Loutfy, and P. S. Vincent. Fluorescence Enhancement from Langmuir-Blodgett Monolayers on Silver Island Films. Langmuir 4 (1998) 518-521.

C. D. Geddes, A. Parfenov, I. Gryczynski, J. Malicka, D. Roll, and J. R. Lakowicz. Fractal Silver Structure for Metal-Enhanced Fluorescence: Applications for Ultra-Bright Surface Assays and Lab-on-a-Chip-Based Nanotechnologies. J. Fluoresc. 13 (2003) 119-122.

C. D. Geddes, A. Parfenov, D. Roll, I. Gryzcynski, J. Malicka, and J. R. Lakowicz. Silver Fractal-Like Structures for Metal-Enhanced Fluorescence Intensities and Increased Probe Photostabilities. C. D. Geddes, A. Parfenov, D. Roll, I. Gryczynski, J. Malika, and J. R. Lakowicz. J. Fluoresc. 13 (2003) 267-276.

A. M. Glass, P. F. Liao, J. G. Bergman, and D. H. Olson. Interaction of Metal Particles with Adsorbed Dye Molecules: Absorption and Luminescence. Optics. Lett. 5 (1980) 368-370.

T. Hayakawa, S. T. Selvan, and M. Nogami. Field Enhancement Effect of Small Ag Particles on the Fluorescence from $Eu^{3+}$-doped $SiO_2$ glass. 74 (1999) 1513-1515.

J. R. Lakowicz, Radiative Decay Engineering: Biophysical and Biomedical Applications. Anal. Biochem. 298 (2001) 1-24.

J. R. Lakowicz, B. Shen, Z. Gryczynski, S. D'Auria, and I. Gryczynski. Intrinsic Fluorescence from DNA Can Be Enhanced by Metal Particles. Biochemical and Biophysical Research Communications 286 (2001) 875-879.

J. Malicka, I. Gryczynski, Z. Gryczynski, and J. R. Lakowicz. Effects of fluorophores-to-silver distance on the emission of cyanine-dye-label oligonucleotides. Anal. Biochem. 315 (2003) 57-66.

Matyushin et al., J. Nanosci. and NanoTech, 4(2004), No 1/2 pp. 98-105.

M. B. Mohamed, V. Volkov, S. Link, M. A. El-Sayed. The 'lighting' Gold Nanorods: Fluorescence Enhancement of Over a Million Compared to the Gold Metal. Chem. Phys. Lett. 317 (2000) 517-523.

V. J. Pugh, H. Szmacinski, W. E. Moore, C. C. Geddes, and J. R. Lakowicz. Submicrometer Spatial Resolution of Metal-Enhanced Fluorescence. Appl. Spectrosc. 57(12):1592-1598, 2003.

S. T. Selvan, T. Hayakawa, and M. Nogami. Remarkable Influence of Silver Islands on the Enhancement of Fluorescence from $Eu^{3+}$ Ion-Doped Silica Gels. 103 (1999) 7064-7067.

K. Sokolov, G. Chumanov, and T. M. Cotton. Enhancement of Molecular Fluorescence near the Surface of Colloidal Metal Films. Anal. Chem. 70 (1988) 3898-3905.

N. Stich, A. Gandhum, V. Matushin, C. Mayer, G. Bauer, T. Schalkhammer. Nanofilms and Nanoclusters: Energy Sources Driving Fluorophores of Biochip Bound Labels. J. Nanoscience and Nanotechnology. 1 (2001) 1-9.

P. J. Tarcha, J. DeSaja-Gonzoles, S. Rodrigesz-Llorente, and R. Aroca. Surface-Enhanced Fluroescence on $SiO_2$-Coated Silver Island Films. Appl. Spectrosc. 53 (1999) 43-48.

D. A. Weitz, S. Garoff, C. D. Hanson, T. J. Gramila, and J. I. Gersten. Fluorescence Lifetimes of Molecules on Silver-Island Films. Optics Lett. 7 (1982) 89-91.

W. Wenselseers, F. Stellacci, T. Meyer-Friedrichsen, T. Mangel, C. A. Baur, S. J. K. Pond, S. R. Marder, and J. W. Perry. Five Orders-of-Magnitude Enhancement of Two-Photon Absorption for Dyes on Silver Nanoparticle Fractal Clusters. J. Phys. Chem. B 106 (2002) 653-6863.

Surface Enhanced Fluorescence: Experiment and Theory Comparison

H. Ditlbacher, N. Gelidj, J. R. Krenn, B. Lamprecht, A. Leitner, F. R. Aussenegg. Electromagnetic Interaction of Fluorophores with Designed Two-Dimensional Sivler Nanoparticle Arrays. Appl. Phys. B. 73 (2001) 373-377.

J. Kummerlin, A. Leitner, H. Brunner, F. R. Aussenegg, and A. Wokaun. Enhanced Dye Fluorescence Over Silver Island Films: Analysis of the Distance Dependence. Molec. Phys. 80 (1993) 1031-1046.

A. Wokaun, Surface Enhancement of Optical Fields Mechanism and Applications. Molec. Phys. 56 (1985) 1-33.

Surface Enhanced Fluorescence: Theory Only, No Experiments

H. Chew. Transition Rates of Atoms Near Spherical Surfaces. J. Chem. Phys. 87 (1987) 1355-1360.

P. Das and H. Metiu. Enhancement of Molecular Fluorescence and Photochemistry by Small Metal Particles. J. Phys. Chem. 89 (1985) 4680-4687.

F. J. Garcia-Vidal, J. M. Pitarke, J. B. Pendry. Silver-Filled Carbon Nanotubes Used as Spectroscopic Enhancers. Phys. Rev. B. 58 (198) 6783-6786.

J. Gersten and A. Nitzan. Spectroscopic Properties of Molecules Interacting with Small Dielectric Particles. J. Chem. Phys. 75 (1981) 1139-1152.

J. I. Gersten and A. Nitzan. Photophysics and Photochemistry Near Surfaces and Small Particles. Surf. Sci. 158 (1985) 165-189.

J. Pendry. Playing Tricks with Light. Science. 285 (1999) 1687-1688.

M. R. Philpott. Effect of Surface Plasmons on Transitions in Molecules. J. Chem. Phys. 62 (1975) 1812-1817.

E. J. Zeman and G. C. Schatz. An Accurate Electromagnetic Theory Study of Surface Enhancement Factors for Ag, Au, Cu, Li, Na, Al, Ga, In, Zn, and Cd. J. Phys. Chem. 91 (1987) 634-643.

BRIEF SUMMARY OF THE EMBODIMENTS OF THE INVENTION

This application discloses the means by which metals and other materials can be physically disposed in combination with other necessary structures to create the needed effect of increasing the fluorescence signal to noise ratio in a form that can be economically manufactured using conventional processes. Embodiments of the invention are means of augmenting the fluorescent signal without substantially increasing the noise in an assay system. Embodiments of the invention are further means that permit robust manufacturing. The specific augmentation means of embodiments of the invention comprises the phenomena of plasmon fluorescent enhancement, resonant optical systems, and optical interference. The plasmon fluorescent enhancement phenomenon is known as metal enhanced fluorescence (MEF), surface enhanced fluorescence (SEF), radiative decay engineering (RDE), or plasmon resonance. Embodiments of the invention structures lead to greatly improved sensitivity in microarray and microplate assays.

Embodiments of the invention are structures for augmenting fluorescent emission from fluorescent molecules which in the most general form comprise the following elements: a solid substrate, an enhancing layer coating the upper surface of the substrate, the enhancing layer comprising an adhesion layer and a nanostructured layer consisting of electrically-conductive, material particularly metal, the nanostructured layer disposed above the substrate and attached to the adhesion layer, the nanostructured surface features having a lateral size of less than about 300 nm. The nanostructured layer may be sealed against contact with aqueous solutions by an aqueous impervious layer, the aqueous impervious layer further serving to assist attachment of subsequent layers. A resonant layer comprising an optically transparent film of specific thickness is disposed above the aqueous impervious layer.

Another general class of embodiments of the invention are realized when a single layer performs the function of more than one of the layers described above. This has the practical value of simplifying the manufacturing process of the product and can result in other superior performance advantages. Specifically, titanium, aluminum, nickel, and alloys of these metals are known to possess high corrosion resistance to saline solutions like those used in assay protocols. They can be used to create adhesion, MEF, and corrosion resistance at the same time. Similarly, the use of "metastable metal oxides", e.g. $AlO_xN_y$ and $TiO_xN_y$ make excellent low-porosity dielectrics and can be used with silver and other nanostructured metals.

In some embodiments, a biologically active binding layer is disposed above the aqueous impervious layer, the biologically active binding layer capable of binding with another biomolecule, that biomolecule normally being specific to a predetermined analyte. In use, a biomolecule labeled with a fluorescent compound can become attached to the binding layer by biological action, thereby placing the fluorescent compound within a predetermined range of distances from the nanostructured layer. In such embodiments the MEF effect increases the fluorescence thereby increasing the sensitivity of the assay.

The objective of embodiments of this invention is to provide practical, robust, and manufacturable structures which use MEF to enhance the sensitivity of analysis and detection of compounds.

Another objective of embodiments of this invention is to provide structures which use MEF to enhance the signal to noise ratio of emitted fluorescent radiation.

Another objective of embodiments of this invention is to provide MEF structures which are resistant to degradation by conditions in aqueous media.

A final objective of embodiments of the invention is to provide structures for determining the concentration of substances in aqueous media which are easy and inexpensive to manufacture and are without deleterious effects on the environment.

DETAILED DESCRIPTION OF THE EMBODIMENTS OF THE INVENTION

The invention is an improved material system that results in augmented fluorescence using a combination of materials, concepts, and structures to achieve a robust and practical design. While scientifically correct and valuable in many cases, the prior art has yet to describe an operational device that can, in fact, be reliably manufactured by those skilled in any of the relevant arts.

Figure 1:
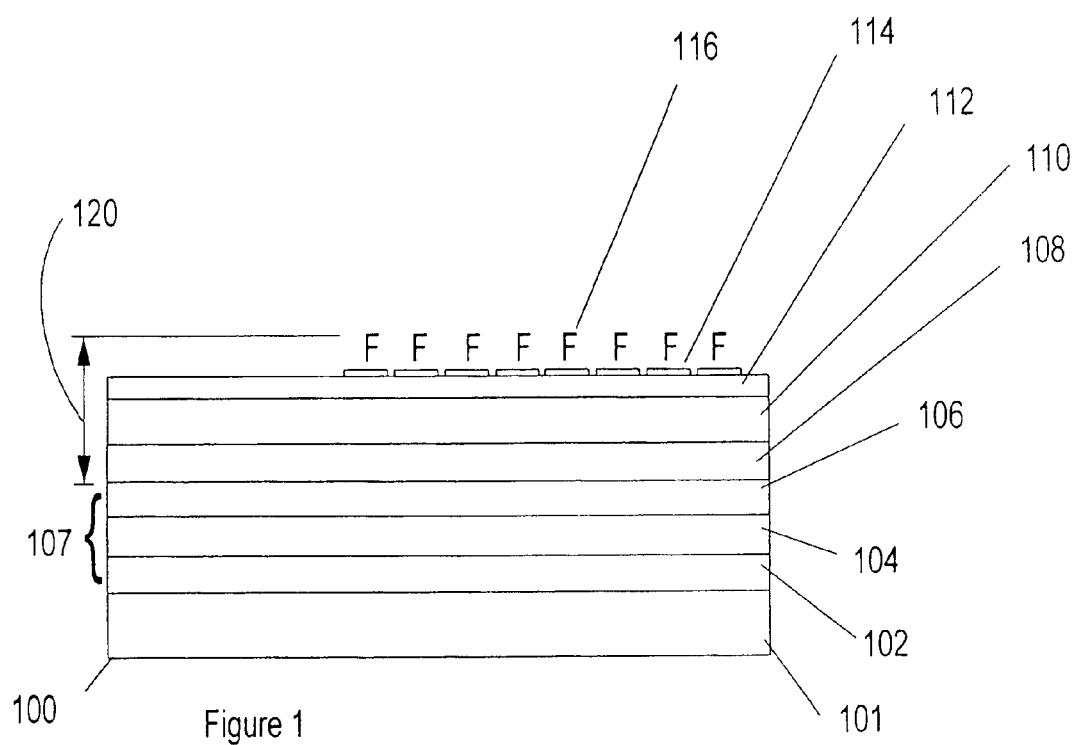
FIG. 1 is a schematic representation of a cross-section of an embodiment of the invention.

FIG. 1 diagrammatically depicts the most general embodiment structure 100. Elements include the interrelated parameters of: substrate 101; an enhancing layer 107, the enhancing layer 107 comprised collectively of an adhesion layer 102, an optional alloy layer 104, and a nanostructured layer 106, the nanostructured layer comprised of electrically-conductive material; an aqueous impervious layer 108; a spacer layer 110; and a binding layer 112, the binding layer having bioactive material or ligands 114 attached to it; and the ligands 114 having the ability to fix or bind a fluorescent molecule 116 to the binding layer 112.

The substrate 101 is comprised of any suitable solid material, such as glass, plastic, quartz, metal such as aluminum or steel. A preferred substrate material is glass. It is not necessary that the substrate be transparent. The substrate may be flat as in a microscope slide or microwell plate or may be in the form of a solid geometric form, such as a sphere, cube, or pyramid.

The enhancing layer 107 is comprised of an adhesion layer 102, optional alloy layer 104, and a nanoparticle layer 106. If vapor deposition is used to fabricate the enhancing layer, the substrate surface must be prepared with an adhesion layer. Titanium, aluminum oxide, tungsten, molybdenum, and chromium are preferred materials for the adhesion layer. The material used for the adhesion layer affects the performance of the system because each dielectric interface in the system has a differing effect on the electrical and opto-physical properties of the system. The only way to ensure optimum performance is through experimentation.

The optional alloy layer 104 also enhances system performance. Suitable alloy layer materials have been found to be palladium, platinum, and nickel. Again experimentation was required to derive the best alloy layer. A preferred specific combination that has been shown to work well involves the application of either titanium, aluminum oxide, tungsten or chromium as adhesion layer.

The nanostructured layer 106 consists of a thin film metal deposited to have a columnar structure with principal surface feature dimensions that matches plasmon resonance at an optical wavelength that is very near to both the fluorescent excitation wavelength and the maximum fluorescent emission wavelength. The most suitable metals include alloys of titanium and aluminum. Other preferred metals are silver, gold, copper, titanium, chromium, tungsten and aluminum, however other metals and alloys yet to be tested may prove to be useful.

The isolation layer 108 is an aqueous-impervious layer which protects the nanostructured layer from degradation associated with aqueous media used in assays. Suitable isolation layers include organic polymers and transition metals of group VIIIB, titanium, and metal oxides, e.g., $Al_2O_3$, $TiO_2$, etc. Further, it is possible in some embodiments of the invention to use metals, e.g., titanium, which have both MEF and resistance to corrosion. The isolation layer is described in greater detail below.

A less general version of the invention, yet one which is most practical and is most preferred comprises a single nanostructured layer of metal alloy that has excellent adhesion, excellent MEF and very high corrosion resistance. Such an alloy can be made using aluminum and titanium in the ratio of about 50 to about 90 atomic percent aluminum. The single nanostructured metal layer replaces layers 102 through 108.

The spacer layer 110 is a layer which provides enhanced fluorescence. Any suitably strong solid material transparent to the excitation and emission wavelengths associated with a fluorescent material used in an assay may be used as a spacer layer. SiO, $SiO_x$, SiN and diamond like carbon are preferred materials for the spacer layer. Other suitable materials include aluminum oxide, titanium oxynitride, titanium oxide, aluminum oxynitride, and aluminum nitride. Each material has properties which effect derivative groups. The method of determining the optimum depth of the spacer layer is described in greater detail below.

In some embodiments the isolation layer 108 is of adequate thickness to perform the functions of the spacer layer 110. In those embodiments there is no separate spacer layer 110. For example, metastable metal oxides such as $AlO_xN_y$, have been shown to be non-porous. Methods of using such materials in the presence of silver are discussed later.

In the case of the preferred embodiment comprising only a single nanostructured layer of metal instead of layers 102 through 108, any spacer material can be used that satisfies the optical and chemical requirements of the intended application. This is because adhesion, corrosion abatement, and MEF are all accomplished using the single preferred alloy so that the resonant spacer layer need not accomplish corrosion protection.

The binding layer 112 has attached ligands 114 which affect biological or chemical binding of fluorescent molecules 116 to the upper surface of the spacer layer. Embodiments of the invention may be applied to all fluorescence based assays, each of which has unique ligand and fluorescent molecule requirements. The "working surface" of the invention is the exposed surface of the binding layer with the ligands. Any and all ligand and fluorescent molecules known or to be discovered can be applied to the binding layer. While the binding layer and subsequent biological layers disposed on the surface of the resonant spacer layer 110 are required in application, the invention is a fluorescence enhancing substrate that is complete without the subsequent assay biology or biological binding surface treatments. Such binding treatments are, in general, the subject of countless other patents.

The total spacer thickness 120 is the combined optical thickness of the aqueous-impervious layer 108, the spacer layer 110, the binding layer, the ligand 114 and the mean location of the bound fluorescent molecule 116.

In practice, embodiments of the invention operate by fixing a fluorescent molecule 116 to a ligand 114 attached to a working surface or binding layer 112 spaced above a nanostructured metallic layer 106. A fluorescent molecule or fluor is any molecule that can be made to fluoresce with sufficient excitation energy. In this patent application, the term "fluor" means such a fluorescent molecule. Reagents, comprising the components of a bioassay, are caused to contact the surface of the binding layer 112 so that fluorescent molecules 116 that usually are attached as labels to an active biomolecule in the reagents, are bound by their active biomolecule to the binding layer 112. This usually occurs by the action of another biomolecule called the analyte that preferentially attaches to both the bioactive material or ligand 114 and to the fluorescently labeled molecule 116. This is one embodiment of the invention that describes one series of biochemical events that comprise one type of bioassay. There are many different series of biochemical events that comprise assays of different types, any one of which ultimately results in a fluorescent molecule being bound in a desired, predetermined proximity to the enhancing layer.

The purpose of embodiments of the assay is to detect a specific predetermined protein or DNA or other molecule which may or may not be labeled with a fluorescent molecule. The system is irradiated with light at an excitation wavelength and the fluorescent light that is emitted is measured. Binding of the fluorescent molecule to the system of this invention results in a great enhancement of the emitted fluorescent light. The biochemical or surface chemistry that accomplishes this is called a fluorescent assay, or just "assay". Embodiments of the invention are systematic structures of material layers which greatly improve the sensitivity, practicality, utility, and manufacturability of devices which accomplish the assays.

There are known theoretical means to calculate the resonant particle dimension for spherical metal particles in free space. The theory available to date does not solve the problem of optimized fluorescence on a surface using a columnar metallic film with more or less hemispherical surface features. It is important to embodiments of this invention that only resonant plasmon structures are involved using the metal structures. The resonant structures are disposed on a substrate surface by any of several known methods adequately described in the literature, such as deposition from aqueous suspension, electrodeposition, precipitation, electron-beam lithography, or vacuum deposition. However, in order to function optimally, the metal layer must be relatively denser than previously described. We have found that a metal layer with an optical density above 2.0 (transmitting less than 1 percent, and which is consequently opaque and highly reflective) is required for best performance of resonant structures of preferred embodiments. By adjusting the deposition conditions, e.g., substrate temperature and deposition rate it is known to those skilled in the arts of thin film deposition that different surface morphologies can be obtained. For preferred embodiments developed so far, we have found that such metal layers are typically greater than 20 nm thick, and are frequently in the range of 60 to 200 nm thick and have surface features with maximum lateral dimensions in the range of 40 to 300 nm.

It is important to embodiments of this invention that the enhancing layer, which comprises the adhesion layer, optionally the alloy layer, and the nanostructured layer must be substantially opaque. We point out that the enhancing layer, adhesion layer, alloy layer, and even the aqueous impermeable layer can functionally all be accomplished with a single layer of the proper metal. One way to accomplish this is to build a rather thick layer of metal with appropriate surface morphology on top of a more or less reflecting adhesion and optionally alloy layers. The preferred method of the invention is to use a single metal or metal alloy deposited at one time to accomplish adhesion, MEF, and corrosion resistance.

A preferred method of depositing the layers in the structure is through use of a vacuum evaporative system. In particular, the model CHA Mark 50 system manufactured by CHA Industries, Freemont, Calif. was used to deposit the layers. The nanostructure size is affected by both the temperatures and the rate of deposition. Higher temperatures resulted in smaller features. When using an evaporator of this type, a preferred substrate temperature of deposition is about 250° C. A preferred rate of deposition is about 0.5 Å per second. Deposition on fused silica (thermal silicon oxide coated silicon wafers) produces a surface structure that provides enhancement in the range of 50.

A second preferred method of deposition of the adhesion, enhancing and spacer layers uses a sputtering deposition process. An AJA 1500-F con-focal UHV sputtering system has been found suitable for this method. In the case of sputtering systems, much like e-beam evaporators, the substrate temperature needs to be controlled to obtain repeatable nanostructure morphology. Also with the AJA sputtering system we have found that structure size can be varied by choice of substrate temperature, however, the physics of the deposition mechanism dictate that sputtering methods, in general, require different temperatures. Depending on the feature size desired, the temperature for sputtering ranges from 25° C. to 250° C.

Figure 2:
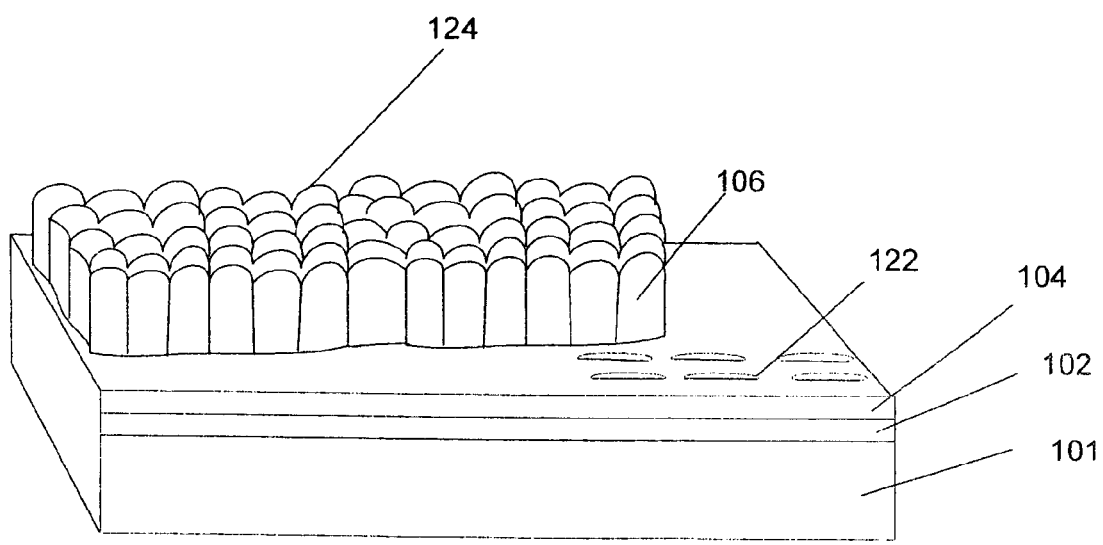
FIG. 2 is a schematic representation of a cross section of the nanostructured metallic film region of an embodiment of the invention.

FIG. 2 is a schematic representation of a cross section of the metallic nanostructured layer of an embodiment of the invention. The elements depicted in FIG. 2 are the same as those in FIG. 1. Referring to FIG. 2, our work has shown that an active metal layer 124 with thickness in the range of 120 nm more or less is required in most resonant embodiments. In particular, the metal layer of the invention has nanostructure resulting from the growth of the metal film layer as one will find predicted in Zone 1 of a Thorton Zone Diagram. Using the relative low gas pressure (~5 milliTorr) and substrate temperatures (less than 150 Degrees C.) employed to make MEF substrates of this embodiment, the bumpy, surface morphology resembles tightly packed nanohemispheres and accompanies a columnar, somewhat porous (on the nanoscale) metal layer. Sparsely populated regions 122 obtained by others using chemical deposition, extremely thin vacuum deposited films or annealed metal films are often referred to as comprising metal island layers or nanoparticle layers, implying discrete metal nanoclusters spaced apart by some distance. Such layers have little enhancing effect in resonant structures of the preferred embodiments. Enhancing particle layers such as region 124 are comprised of a more or less columnar growth of metal 106 which creates the desired dense nanostructure film. When viewed with a scanning electron microscope or atomic force microscope for example, the "surface morphology" suggests a particle layer. In fact particle layers are not necessarily required, and the typical columnar formation of metal crystals provides exceptional MEF performance particularly when used with a resonant spacer layer.

It is understood that the aim of the invention is to create enhanced fluorescence using plasmons, and that the surface morphology that is detectable using nano-imaging tools is the only available metric of the structure resulting from the deposition protocol. The surface appearance does not necessarily reveal the underlying metal structure, but does provide a means of correlating the process results, in terms of "feature diameter" to the achievement of high enhancement. Using such imaging tools, which image only the top of the surface, it is convenient to refer to the bumpy irregularities in the nanostructured surfaces as "particles" or as nanohemispheres even though they are not discrete particulate entities. Therefore reference herein to "particles" includes any surface that appears to have a bumpy, more or less nanohemispherical form that suggests a particulate layer. The term "nanohemisphere" refers to the irregular bumpy surface features which essentially completely covers a surface. The "diameter" of a nanohemisphere means the linear measurement from one edge of a nanohemisphere to another edge taken across the center of the nanohemisphere. The "circumference" of a nanohemisphere is not necessarily a circle, and the surface is not necessarily a hemisphere in cross section.

Not shown in FIG. 2 is the aqueous-impervious layer. In practice that layer, if used, is a conformal coating of relatively uniform thickness over the metal nano layer. In this case, an amorphous, substantially pore free, surface is desirable and can be accomplished using some dielectrics mentioned herein and also by using a thin deposition of a corrosion resistant metal such as titanium, palladium, gold, nickel, and others, or metal alloys such as aluminum-titanium before the dielectric coating is applied. When deposited in layers less than about 20 nm thick, such metals create a substantial barrier to corrosion and very little or no degradation of the MEF effect of the underlying nanostructure of silver. Novel in such embodiments is the use of a metal corrosion resistance interlayer. Most optical structures use transparent, non-conductive materials to protect metallic surfaces, but for plasmon enhancement, a thin metal barrier layer can be used to prevent corrosion.

The resonant size of the surface features is the diameter of a particle which gives optimum fluorescence enhancement. When radiation in the visible spectrum is involved, the resonant size ranges from 50 nm to 200 nm. Widely used fluorescent compounds Cy3 and Cy5 use laser excitation wavelengths of 543 nm and 633 nm, respectively. The optimum resonant particle size for Cy3 was found to be 80 nm to 90 nm. The optimum resonant particle size for Cy5 was found to be 90 nm to 130 nm. The exact resonant size was found to depend on the active metal material properties and the dielectric environment surrounding the surface features. This can only be found empirically. On the other hand, films made with a broad distribution of feature sizes were found to have a relatively broad range of nominally wavelength-independent enhancement. Such films offered less enhancement in a specific excitation band than films with narrower distributions of particle sizes.

In general, the augmentation factor is defined as the emitted fluorescence intensity from a metal enhanced fluorescent (MEF) region divided by the emitted fluorescence intensity from a non-MEF region of a given substrate or similarly prepared reference glass surface. MEF occurred because the plasmons associated with the nanostructured layer of metal couples energy into and out of a nearby fluorescent molecule. The wavelength of light coupled into the fluor is that of the excitation light. The wavelength of the energy coupled out is the wavelength of the emission light.

Considering the plasmon enhancement theory based on single spherical particles, in each case the augmented electrical field associated with input and output energy is a function of the wavelength and other parameters according to Equation 1.

$$E_T = F_{Ex}(\lambda_{Ex}, d, \phi_{Ex}, T, Q_\lambda) + F_{Em}(\lambda_{Em}, d, \phi_{Em}, T, Q_\lambda) \qquad 1.$$

where, $E_T$ is the total enhanced electrical field, $\lambda_{Ex}$ is the excitation wavelength, $\lambda_{Em}$ is the emission wavelength, d is the spatial density of particles, $\phi_{Ex}$, $\phi_{Em}$ are the optimum diameters of the particles associated with excitation and emission wavelengths, T is the total spacer thickness, and $Q_\lambda$ is the quantum yield of the flour at the excitation wavelength. If factored from the generalized form of Equation 1, the optimum diameter $\phi$ of the particle is a function of two wavelengths. The best choice of particle diameter therefore is somewhere between $\phi_{Ex}$ and $\phi_{Em}$. This diameter can realistically only be found experimentally.

Regarding particle spatial density, in contrast to conventional structures, we have found that it is not sufficient to have an arbitrarily sparse population of particles, as indicated in FIG. 2 by the region 122. The spatial density of particles must result in a very high optical density. This cannot be accomplished by "islands spaced apart," "touching", or connected by arbitrary amounts of the same materials as suggested by others. The desired very high optical density was accomplished by the deliberate control of metal disposition on the substrate surface so that resonant features with total layer thickness of about 120 nm create a substantially opaque film.

Deposition parameters used to accomplish this desired geometry of surface features vary among different vacuum deposition machines and wet chemical process. It is necessary to experimentally calibrate the deposition process to obtain both the desired particle diameter, thickness, and spatial density. One preferred means for quickly calibrating the process is shown with reference to FIGS. 3A, and 3B.

Figure 3A:
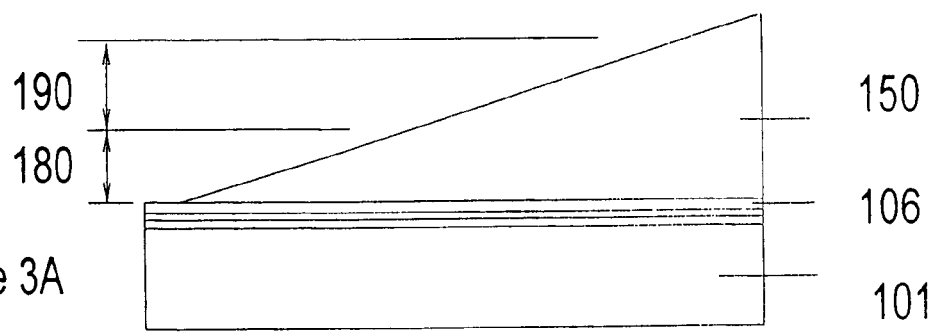
FIG. 3A is a schematic representation of a cross-section of an embodiment of the invention with a gradient spacer layer.
Figure 3B:
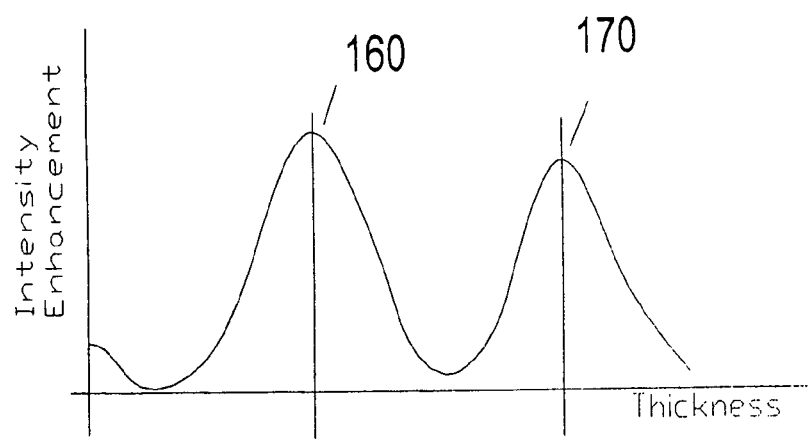
FIG. 3B is a graph showing the fluorescence intensity enhancement associated with certain spacer layer thicknesses.

FIG. 3A is a schematic representation of a cross-section of an embodiment of the invention with a gradient spacer layer with the intensity enhancement over the varying thickness of the spacer shown in FIG. 3B. Visible in FIG. 3A is the substrate 101, the nanostructured layer 106, and a wedge-shaped spacer layer 150. In the case depicted in FIG. 3A, a peak of intensity enhancement was noted at the area corresponding to a spacer thickness represented by 180; and another peak of intensity enhancement at the spacer thickness represented by the sum of the thicknesses 180 and 190.

FIG. 3B is a figure showing the relative intensity enhancement at various points in systems with gradient spacer. Peaks of intensity enhancement are shown at 160 and 170.

A preferred method of determining the in-situ optimum spacer thickness for a given assay application involves fabricating a spacer layer having a linear thickness gradient or other deliberate and known thickness variation above the metal film 106. The vertical dimensions in FIG. 3A are greatly exaggerated. In practice the gradient spacer layer will have a thickness ranging from about 0 nm to about 400 nm.

In the example illustrated in FIGS. 3A and 3B the thickness ranges over sufficient distance to encompass two regions of maximum energetic coupling shown by the peaks of intensity enhancement 160, and 170, at thickness 180 and 190 respectively. Using evaporation or sputtering deposition and suitable fixtures this gradient spacer film shape can be built in a relatively short time with substantial accuracy obtained using a crystal oscillator deposition thickness gage in the deposition chamber, coupled with a timing mechanism that permits the user to relate the deposition time to a given thickness. For example, a device can be built that moves a shutter linearly across the substrate at a known speed during the deposition process. The position of the shutter can be made available electronically from a linear displacement encoder inside the vacuum chamber, and the parameters of time, distance, and thickness can be plotted for use in the subsequent processes with that particular vacuum deposition setup.

It is important to note that different deposition systems are likely to have slightly different calibrations. Following the deposition of the gradient spacer layer, the thickness of the layer should be verified with an independent nanometrology instrument such as film thickness gage or ellipsometer. Once the gradient substrate is accurately characterized, a thin film of a suitable fluor can be evaporated onto the surface thus providing an extremely uniform coating. Then using a standard microarray reader the fluorescence intensity can be measured at many points across the surface of the substrate. These data contain and reveal: the statistics of point-to-point enhancement uniformity over the entire substrate surface which relates to the uniformity and size range of the cluster dimensions in the particle film; the enhancement versus distance layer thickness; and the timing of the deposition process required for optimum performance. Moreover, this single measurement device and method characterizes and reveals many of the important process parameters required for optimum manufacturing.

It is apparent from the literature and is illustrated in FIGS. 3A and 3B that there are multiple regions of peak energetic coupling as in 160 and 170. This fact is used in the manufacturing process. It is possible to use the gradient substrates to determine the optimum thickness for pairs of fluors, such as Cy5 and Cy3 which are often used in combination in assays. By determining the correct thickness for the spacer layer and correct feature size, fluorescent enhancement has been simultaneously optimized for two or more fluors.

In another preferred case, the embodiment is fabricated so that the peak enhancement is chosen to occur at the second or third intensity enhancement peak.

This permits the use of a thicker spacer layer which has two advantages. The thicker spacer layers tend to be more robust mechanically. The enhancement is less sensitive to variation in spacer thickness in the thicker cases, thus relaxing manufacturing tolerances of the distance layer and improving the overall uniformity of the assays.

The resulting system of materials, with distance layer thickness chosen to correspond to an energetic coupling peak (as measured by enhancement) is, in fact, a multiply resonant structure. Others have built very similar appearing structures in which a mirror layer of continuous metal, (not nanostructures) is deposited on a substrate followed by an optically transparent layer ¼ wavelength thick above the mirror layer. This layer comprises a resonant layer in the sense that constructive interference of the excitation wavelength can be made to occur at the top surface thus increasing the optical intensity available to excite fluors attached to that surface by roughly a factor of 4. The more or less isotropic fluorescence emitted from the fluor molecule is also made to reflect from the mirror surface redirecting half the emitted energy back toward a detector placed above the surface. This yields a total enhancement of about 8 fold.

The use of a resonant layer in the case of embodiments of the invention functions by a different mechanism. In the embodiments of the invention, the spacer layer mutually resonates with the excitation and the particle plasmon in a manner to pump more energy into the plasmon, which in turn is energetically coupled to the fluor.

The selection of the correct thickness of this resonant layer is not exactly ¼ of the excitation wavelength, but is dependent upon the complex dielectric properties of the protected metal surface, and the upper surface of the spacer layer. Again, there are no existing closed form mathematical solutions that predict the exact layer thickness to accomplish the desired plasmon field resonance, but a calibration method discussed relative to FIGS. 3A and 3B does suffice to ensure that the manufacturing process is properly tuned for optimum resonant enhancement. The distinction between the function of this resonant layer, and all others, is that it accomplishes fluorescence enhancements in the range of 40 fold and more, greatly exceeding anything possible with interference effects. Embodiments of the invention are tuned systems in which each component plays a critical role. While the system can only be optimized as a system, the properties of the individual components each must be chosen to result in the optimum system.

Embodiments of the invention are used in bioassays that must withstand exposure to corrosive chemicals and mechanical trauma. Assays require elevated temperatures, formamide/water solutions, sodium citrate, detergents such as SDS (sodium dodecylsulfate), ethanol, isopropyl alcohol, solutions of succinic anhydride, boric acid, phosphate buffered saline, hydrochloric acid and other materials that can be corrosive. Microarrays are also spotted using very sharp pointed metal pins that come into contact with the surface with substantial pressure. Considering the mechanical and chemical durability of the substrates, it has been found that vacuum deposited silver particles are very susceptible to chemical attack.

Annealing the silver particles resulted in reduced sensitivity to chemical attack. Nevertheless, for microarray, microplate, and all two-dimensional surface embodiments, the chemical protocols commonly used to perform assays destroy the substrates built by conventional methods within a matter of minutes. Corrosive material can leak through nano or micro pores in the spacer layer and can also attack the exposed edges of the substrate. Therefore any embodiment built according to conventional methods will experience premature failure.

Others have conjectured that the spacer layer, biorecognitive layer, binding layer, or distance layer will serve to protect the metal nanostructures beneath it. This overlooks the fact that assays are routinely submerged in baths of acidic, basic, and saline solutions, often for extended periods. This ensures that liquid has access to the sides of the substrate as well as to the top and bottom. We have found that clean room procedures can result in relatively nanopore free spacer layers, but typical spacer layer materials such as SnN, ZnO, SiO, SiOx, diamond like carbon, MgF, etc. do not seal adequately at the edges and generally all metal oxides have surface porosity, with the exception of meta-stable metal oxides. Consequently, a robust embodiment of the invention requires either the use of a metal that resists corrosion in assay conditions or it requires the application of a material which completely protects the metal, particularly when silver is used, before the spacer layer is applied. Successful means of protecting the silver surface from chemical attack during actual use and protection of the silver surface from process steps are closely related aspects of the methods of this invention. It is known that so-called meta-stable metal oxides (e.g., $AlO_xN_y$, $TiO_xN_y$) are substantially pore-free amorphous dielectrics that are used to withstand extremely harsh corrosive environments. These can be deposited using the process of reactive sputtering requiring the presence of oxygen in the deposition plasma gas. Oxygen plasmas erode silver. Therefore the problem with using these reactive sputtered oxides is that the silver does not survive. To prevent erosion of the silver, embodiments of the invention applies a thin (2 to 10 nm) layer of titanium metal directly on the silver to prevent oxidation of the silver. Palladium has proven to be effective. We expect that several other materials can be used and will be explored in future development. This is discussed below.

Protection with a self-assembling monolayer of molecules including thiols, phosphines, phosphates, amines or carboxyl-compounds as monomers, or more desirably, as polymerized layers are useful alternatives, however, the use of these presently requires removal of the substrate from the vacuum system, exposure to dirt, increased handling costs, etc. so, while we have proven the viability of these materials, they are not presently preferred.

The application of these types of protection has been shown to be preferred when using silver and is useful for embodiments using gold nanostructures as well. This is because the entire system is subject to attack including the adhesion metals or materials as well as the active particle plasmon generating material such as silver or gold. While gold resists corrosion quite well, adhesion metals do not. In some embodiments or for some applications it may be necessary to seal the substrate around the edges using any readily applied sealing material that resists corrosion and adheres to the substrate.

In some embodiments a region of the top planar surface of the substrate is masked prior to the deposition of the active metal layer. The mask is removed after deposition of the metal layer. The top surface then is coated as described above with an aqueous impervious material and the manufacture of the structure is completed as above. In such an embodiment a sharp edge of the nanoparticle layer is overlapped by the aqueous impervious layer and the spacer layer. Such an embodiment allows determination of the distinction between the fluorescent emission from an enhanced region and a non-enhanced region of the substrate.

In some embodiments in which a portion of the top planar surface of the substrate is masked prior to the deposition of the nanostructured layer, the mask is configured to cover a narrow peripheral band about the top outer boundary of the planar substrate. After deposition of the nanostructured layer on the substrate the mask is removed and the structure coated with aqueous impervious material and the manufacture of the structure is completed as above. In these configurations the edges of the nanostructured layer are sealed by the aqueous impervious layer, thereby preventing intrusion of aqueous solutions into the nanostructured layer.

In some embodiments the aqueous impervious material is also used as the spacer material. In these embodiments the aqueous impervious layer 108 of FIG. 1 and the spacer layer 110 of FIG. 1 are combined in a single aqueous impervious layer with the thickness of a spacer layer. Certain polymer and vacuum deposited dielectric materials are suitable for performing the combined aqueous impervious and spacer layer functions.

Embodiments of the Invention

Substrates Tuned for a Specific Fluor

Many different fluors are used in fluorescence-based bioassays. Fluors are usually excited using a narrow-band source such as bandpass filtered or laser light. This is done to simplify the task of filtering the excitation light from the emitted fluorescence. Lasers can be purchased for a limited set of specific wavelengths. One usually chooses a laser that emits light as close as possible to the peak of the fluor's absorption spectra. The multilayer substrate system is fabricated to be "resonant" as described in the discussion of Equation 1 above.

Table 1 provides examples of the tuned structures required for four popular fluors. Each of these table entries represents a specific embodiment of the invention. Particle dimension, elsewhere called particle diameter φ, refers to the mean particle size in an optically reflective layer of particles having a statistical distribution of sizes centered, more or less, on the size indicated in the table. Similarly, index of refraction measurements are approximate. Structures built that obey the dimensions indicated in Table 1 using adhesion layers of tungsten followed by palladium exhibit repeatable enhancement in the range of 20 fold and more.

TABLE 1

| | Approximate Particle Size and Total Spacer Thickness Tuning | | | | | | |
|---|---|---|---|---|---|---|---|
| Fluor | Excitation nm | ¼ wave Optical | ¾ wave Optical | Spacer Index of Ref. | ~¼ wave Physical | ~¾ wave Physical | Particle Dimension nm |
| Europium | 340 | 85 | 255 | 2.47 | 34 | 103 | 64 |
| Rh6g | 514 | 128.5 | 385.5 | 2.42 | 53 | 159 | 97 |
| Cy3 | 543 | 135.75 | 407.25 | 1.96 | 68 | 204 | 103 |
| Cy5 | 633 | 158.25 | 474.75 | 1.93 | 82 | 246 | 120 |

Referring to FIG. 1, the total spacer thickness is the combined optical thickness of all materials between the surface of the metal film and the "mean" fluor location above the surface of the spacer layer. In the simplest case, the chemical isolation layer 108 in FIG. 1 is a molecular monolayer having thickness in the range of 0-2 nm. The spacer material, SnN, ZnO, SiO, SiOx, MgF, DLC, AlO$_x$N$_y$, etc., is applied to a physical thickness that is empirically chosen as exemplified in Table 1. The physical thickness is the thickness measured by the deposition process metrology equipment. Since all optically transparent solid materials have index of refraction greater than one, the actual optical path length, or "optical thickness", of the layer is the physical thickness multiplied by the refractive index of the material.

Similarly, the feature dimension is chosen to accomplish plasmon resonance as described above. While it is possible to calculate the resonant dimension of a spherical particle in free space, it is not possible, using any theory presently available, to calculate the resonant dimension for a layer of surface features according to embodiments of the invention. In practice, this dimension is found using repeated deposition experiments in which either deposition rate, substrate temperature during deposition, or both, are varied to yield features of different sizes. These features are subsequently tested using the methods of FIGS. 3A and 3B to arrive at an optimum value.

For any given feature size and excitation wavelength there will be peaks 160, 170 in the curve of enhancement versus total spacer thickness shown in FIG. 3B. The height of those peaks reaches maximum value when the feature size is optimally chosen for the excitation and emission wavelength used and the spacer thickness, as suggested by Equation 1. When this condition is accomplished, enhancement of fluorescence in the range of 20 to 200 times has been found. Such fluorescence enhancement is unique to embodiments of this invention.

Structures Using Multiple Layers of Dielectric

Another embodiment involves planar or non-planar substrates in which the spacer layer comprises multiple substances. If the spacer layer is composed of N materials, the jth of which has refractive index I$_j$, and thickness T$_j$, the total optical thickness T is:

$$T = \sum_1^N T_j I_j. \qquad 2$$

This is particularly important in embodiments employing specialized biorecognitive surfaces deposited on the top of the spacer film. It is important to ensure that the optimum conditions for the chemical assay reaction on the surface of the apparatus be maintained. For example, a conventional spacer layer, SnN, is highly hydrophobic and does not permit stable chemical binding of DNA and protein. Surfaces that have been treated to be compatible with biochemical bonds are called functionalized surfaces. Many dielectric materials, e.g., MgF and SnN do not permit functionalization without extraordinary chemical processing. A surface previously taught to be useful, ZnO has been found to be too soft for use in practical assays. Spacer layer materials SiO, SiOx, SiN, diamond like carbon (DLC), AlO, Al$_2$O$_3$, AlO$_x$N$_y$, and titanium oxinitride have been discovered to be readily functionalizable and mechanically robust and are preferred for use in embodiments of the invention.

In some cases the functional layer, or biorecognitive layer, has substantial thickness. In these cases the index of refraction of the biorecognitive layer can only be determined after the layer is in place. Materials such as nitrocellulose and other polymers may be used as a component of the spacer layer. In each case a specific set of thicknesses must be experimentally determined.

Further, embodiments of the invention may be used in a wet environment. The following discloses an embodiment in which the substrate is the bottom of the wells in a microplate. Assays in microplates are performed in solution. In those cases the biorecognitive layers that bind the fluors to the spacer surface have varying thickness and their indexes of refraction are rather low, approaching that of water. These distances can all be accounted for in Equation 2. Only when all material thicknesses are properly disposed will the substrate provide optimum fluorescence enhancement and robust stability.

Structures Tuned for Two or More Fluors Simultaneously

The feature size and spacer thickness may be selected to accomplish substantially optimum and similar enhancement of two or more fluors in the same assay. This is important in assays that involve the ratio of fluorescence emitted at two different wavelengths. Typically Cy3 and Cy5 are used for these assays, although many other dyes are used. In these embodiments only one uniform spacer thickness has been used over the entire surface of the substrate. In another embodiment various segments of the substrate may have spacer thicknesses of varying thicknesses.

The location of the resonant peak of fluorescent enhancement with respect to total spacer layer thickness has been found to be a function of both feature dimension and excitation wavelength. For example, it was found to be possible to excite Cy5 at 633 nm and at 543 nm and obtain enhancement peaks of different amplitude at different thicknesses of the spacer layer. In the case of a 2-dye substrate, it is desired to have a predetermined amount of enhancement for each dye. It has been found possible to excite Cy5 at 543 nm, and adjust the amplitude and location of the enhancement peak by changing the particle size.

Figure 4:
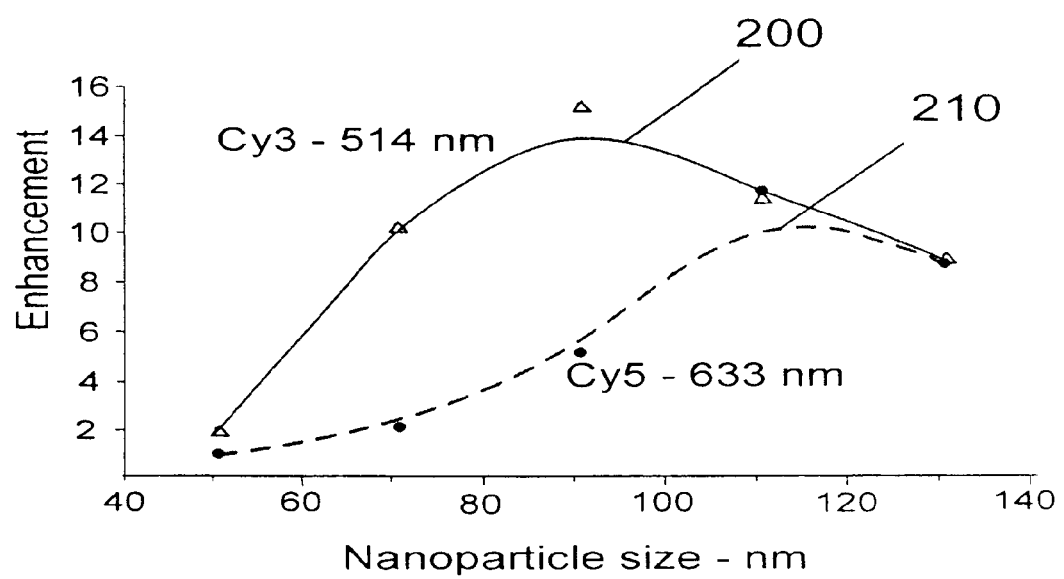
FIG. 4 shows the relationship between nanoparticle size, excitation wavelength, and fluorescence enhancement for two fluorescent materials.

FIG. 4 illustrates that the peaks of fluorescent enhancements with respect to excitation wavelength for two dyes, Cy3 and Cy5, occur at different feature sizes. In the experiments shown in FIG. 4 the spacer thickness was held constant. For Cy3 excited at 514 nm (triangles) the enhancement peak 200 occurred at particle diameter of 90 nm. For Cy5 excited at 633 nm (circles) features of about 112 nm diameter provided maximum enhancement 210. FIG. 4 indicated that the enhancement peak was a function of feature size.

Figure 5A:
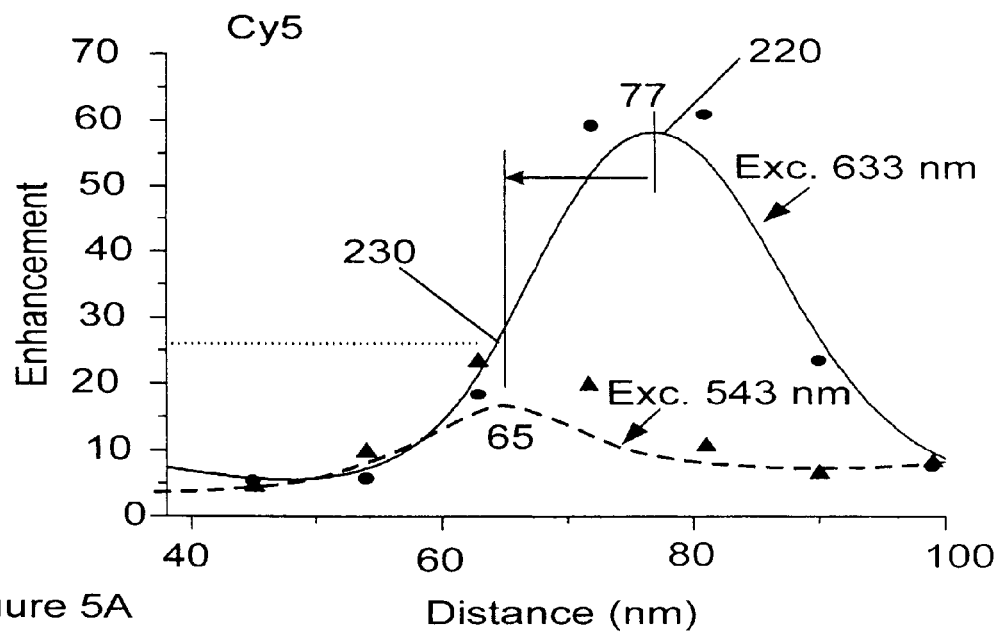
FIG. 5A shows the effect of excitation wavelength and particle size on two fluorescent materials.

FIG. 5A shows the relationship between fluorescence enhancement of Cy5 excited at 543 nm (triangles) and at 633 nm (circles) and spacer thickness using features of about 112 nm diameter. Excitation at 633 nm produced an enhancement peak 220 at a spacer thickness of 77 nm. Excitation at 543 nm produced an enhancement peak 230 at spacer thickness of 65 nm.

Figure 5B:
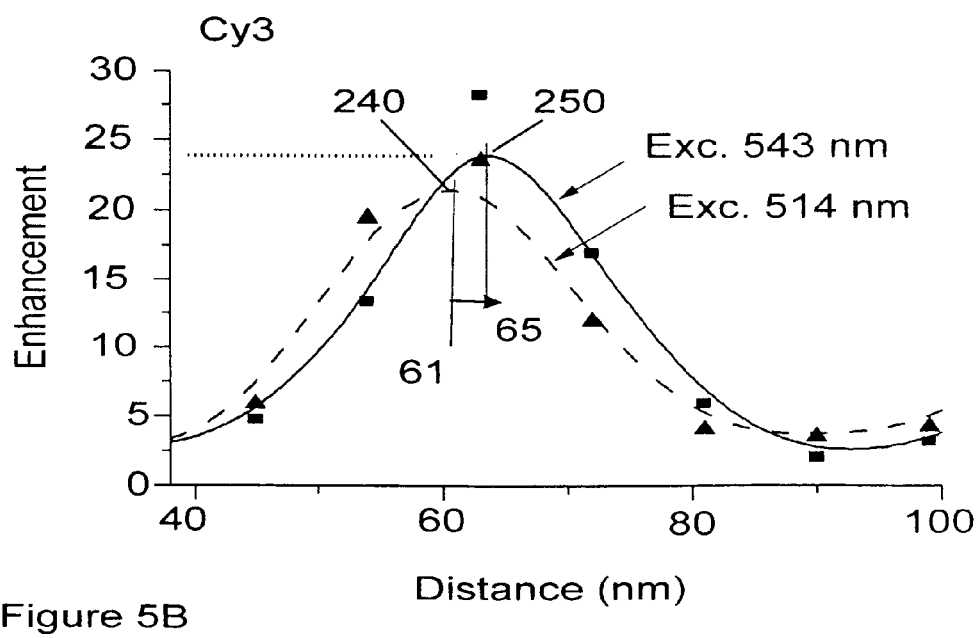
FIG. 5B shows the effect of excitation wavelength and particle size on two fluorescent materials.

FIG. 5B shows the relationship between fluorescence enhancement of Cy3 excited at 514 nm (triangles) and at 543 nm (circles) and spacer thickness using features of about 112 nm diameter. Excitation at 514 nm produced an enhancement peak 240 at a spacer thickness of 61 nm. Excitation at 543 nm produced an enhancement peak 250 at 65 nm.

The experiments shown in FIGS. 5A and 5B showed that in a system using features of about 112 nm and excited at 543 nm, both Cy5 and Cy3 exhibit enhancement of about 25 fold at the same spacer thickness, 65 nm.

In general substrates are made to have only uniform spacer thickness. Since it is known that the resonant peak location as a function of thickness is a function of feature size and excitation and emission wavelengths, it has therefore been shown that approximately equal enhancement of two dyes on one substrate using one spacer thickness can be obtained.

It can be appreciated that there are many combinations of material parameters that effect this same or similar phenomenon. The index of refraction determines the optical thickness of the spacer layer. If a low index spacer material is chosen, e.g., a polymer or low index glass, the spacer must be thicker than if a high index material, such as $Sn_xN_y$ is used. The x and y subscripts used here indicate that in a vacuum deposition process non-stoichiometric ratios of materials may combine to produce the film. Each combination may have a different index of refraction that can be controlled and predetermined in the manufacturing process.

For a low index material, variations in material properties and deposition thickness have a smaller effect on the extent of the enhancement factor. The enhancement peak was found to be broader when low index spacer material was used. Therefore it may be desirable to use low index spacer material in the case of single or multi-dye assays because uniformity of the performance of the product is easier to control. Judicious choices of materials are clearly necessary, however, to ensure robust structures.

Structures Using Chemically Resistant Metals and Alloys

Another general class of embodiments of the invention are realized when a single layer performs the function of more than one of the layers described above. This has the practical value of simplifying the manufacturing process of the product and can result in other superior performance advantages. Specifically, titanium, aluminum, nickel and alloys of these metals are known to possess high corrosion resistance to saline solutions like those used in assay protocols. Nanostructured surfaces of these metals, as well as chromium and palladium have the potential to produce MEF. Further, titanium and chromium are commonly used to create adhesion layers as described above. Thus either of these metals might be disposed in a structure that accomplishes three of the functions of the several independent layers described above: adhesion, MEF, and corrosion resistance. We have demonstrated MEF exceeding 4-fold using titanium and titanium-aluminum alloys with $TiO_2$ and $Al_2O_3$ spacer layers. Both of these have proven to be resistant to 20×SSC buffer solution for many days in complete submersion tests. These are ultimately reliable and stable product embodiments using materials generally not discussed in the literature.

While silver is still the material giving the highest MEF proven in our experience, combinations of silver and Ti, Ni, Cr, and Al are also within the scope of future development foreseen in this invention. For example, Ti—Al alloys, (such as 15% Ti-85% Al) exhibit MEF in the range of 4 or more and resist 20×-SSC for many weeks. We have also built nanostructured aluminum slides and measured MEF in excess of 10 with an $AlO_xN_y$ dielectric. Al has the advantage that oxidation of the surface self limits, meaning, aluminum oxide formed on the surface of bare aluminum creates a barrier to further oxidation. When done in a controlled manner, a surface that resists chemical attack can be achieved.

As a further example using Ti as an adhesion material, we have made a structure comprising Ti (2 nm thick), nanostructured Ag (120 nm thick), Ti (2 nm thick). The lower layer of Ti acts as the adhesion layer. The upper layer of Ti is the protective layer upon which dielectrics such as $Al_2O_3$, $AlO_xN_y$, $TiO_2$, and $TiO_xN_y$ can be deposited. The $AlO_xN_y$ and $TiO_xN_y$ compositions provide excellent chemical resistance. The top Ti layer protects the silver from oxidation during a reactive plasma deposition (sputtering) of $AlO_xN_y$ or $TiO_xN_y$. Similarly, $Al_2O_3$ can be used in place of Ti for both adhesion and protection from oxidation during the reactive sputtering step that accomplishes a chemically impervious dielectric layer. These are proven examples of embodiments of the invention possessing both adequate enhancement and chemical resistance. Such forms are not revealed in the literature. Other unique material combinations yet to be experimentally determined are foreseen in the invention.

Further, the process step of using a thin layer of e.g., Ti, Si, Al, $SiO_2$, Pd, Au, $Al_2O_3$, $TiO_2$, and other materials to protect a nanostructured silver layer from oxidation during the reactive deposition of a non-porous dielectric such as $AlO_xN_y$ is not taught elsewhere and has the novel advantage of permitting a non-porous chemically resistant dielectric to be formed on silver.

Structures Made Using Periodic Arrays of Particles

Figure 6:
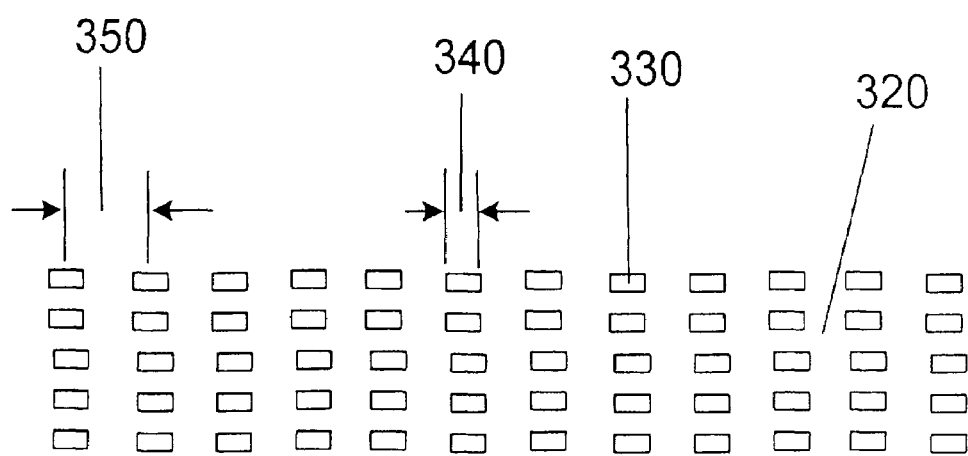
FIG. 6 is a diagrammatic representation of the generalized periodic structure of nanoparticles.

FIG. 6 is a diagrammatic representation of the generalized periodic structure of particles. FIG. 6 illustrates a top view of generalized periodic arrangement 320 of nanoparticles 330. In such embodiments in the visible spectral range the particle sizes 340 are also in the range of about 50 to 150 nm. Larger particles are useful at IR wavelengths. The center to center distance 350 of the particles, the thickness of the particle, the geometrical pattern or shape of the particle, the spacer optical thickness and the "resonant dimension" of the particle all combine to affect the ultimate enhancement factor. Experimentation with square and triangular shaped silver particles showed that particles in the size range of 110 nm to 130 nm were most effective at excitation wavelength of 663 nm. It is likely that a resonant spacing distance for the particles is related to the dimensions of the particle and the dielectric constants of the surrounding materials. Periodic arrays of metallic particles can be made using self-assembly, nanoimprint lithography, and conventional lithography for features within the size limits of lithographic methods used in the semiconductor industry.

Periodic structures have been made on silicon semiconductor wafers coated with $SiO_2$. In these cases the optical density of the periodic silver structure is not as great as that of other embodiments and the nanoparticles layer is sparsely populated as compared to other embodiments of the invention. The enhancement in this embodiment possibly is aided by the reflective properties of the silicon wafer and by resonant interactions of the periodic structures.

Embodiments in Microplates

Figure 7:
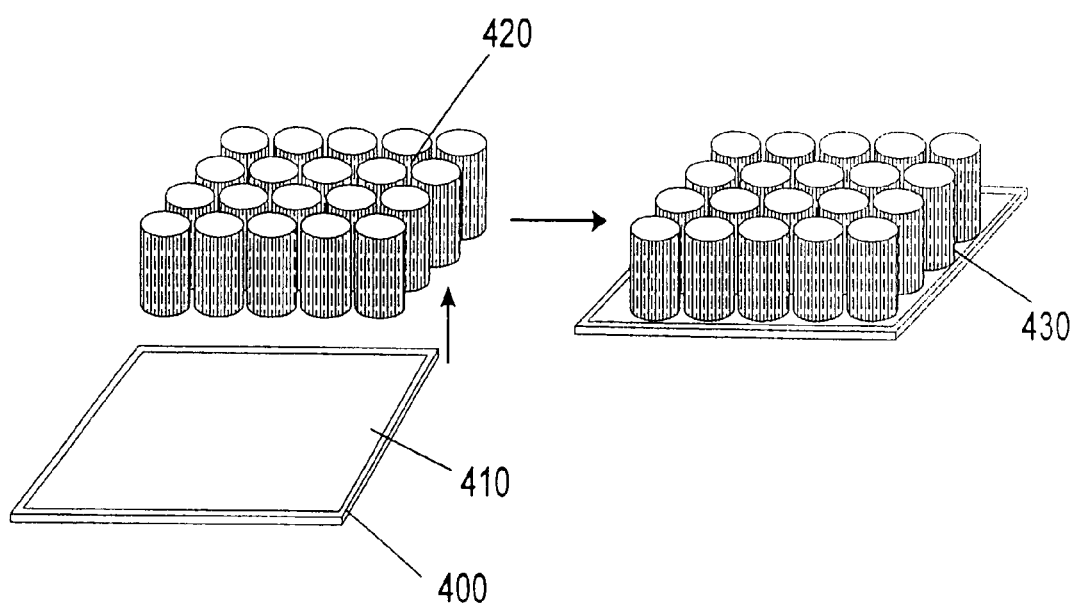
FIG. 7 is a diagrammatic depiction of the manufacture of a microwell embodiment of the invention.

FIG. 7 shows an embodiment of the invention using microplates. Microplates are arrays of small containers or wells commercially available as 96, 384, 1536 well assemblies. The wells may be cylindrical or otherwise shaped to contain a small volume of liquid. A microplate typically measures about 3 inches by 5 inches. The bottom of the wells can be coated with multiple layers of materials to form a resonant enhancing substrate using the same design as microarray substrates. The easiest embodiment of this design is accomplished by first coating, according to the invention, a planar bottom plate 400 made of glass or plastic. It will be appreciated that coating this plate is substantially the same as coating a substrate as in FIG. 1. The well array 420 is constructed without bottoms to the wells. Once the bottom plate is coated with a MEF surface treatment 410, the bottom plate is attached to the bottom of the well array assembly 430. All descriptions and technical considerations for previous embodiments of the invention apply to the microplate embodiment.

MEF for Electrophoresis Plates

Electrophoresis is a well known and widely used method of protein and DNA analysis. In the process, a gel is sandwiched between two glass plates and protein or DNA molecules are separated using a strong electric field to force the migration of the molecules through the gel. A molecule's properties determine how rapidly an electric field can move the molecule through a gelatinous medium. Bands of molecules with similar size and charge form in discrete longitudinal locations along the length of the gel plate. The molecules can be labeled with fluorescent material to resolve situations when each band might contain more than one type of molecule. Hence a band might contain 3 or more colored fluors. Of particular interest is the case when a very few number of molecules of a single specific type (color) form a band, but the raw fluorescence signal is too weak to detect. Such molecules could be, for example, very weakly expressed disease markers.

If the bottom plate is made in the manner of a MEF substrate described herein, very weak fluorescence can be enhanced and rare molecules can be detected. To best accomplish this the bottom plate is prepared as a MEF surface. Once the bands of molecules have formed in the conventional manner, comprising molecules vertically disposed throughout the thickness of the gel, an electric field is impressed normal to the planar surface in a manner to force the vertically disposed molecules into close contact with the MEF-surface plate. The gel can then be removed the MEF plate can be scanned using enhanced fluorescence.

Substrate Designs Affecting Both Fluorescent Intensity and Fluorescent Lifetime

It is known that MEF has the effect of increasing fluorescence intensity. In close proximity to the metal surface, fluorescence intensity changes very rapidly with very small changes in distance. This region is not useful for stable microarray designs because it is very difficult to control the separation distance sufficiently to ensure repeatable performance. The biology itself can create variations of several nanometers which can result in large changes in enhancement. In this region MEF also causes very large changes in the fluorescence lifetime. That fact can be very useful in designing a multilayer structure for what is known herein as phase mode fluorescence assay detection. This is most readily appreciated in the case of a homogenous assay conducted in a fluid volume, e.g., using a microplate embodiment of the invention. In this case the assay is conducted in fluid in either a homogeneous or heterogeneous assay format.

Figure 8:
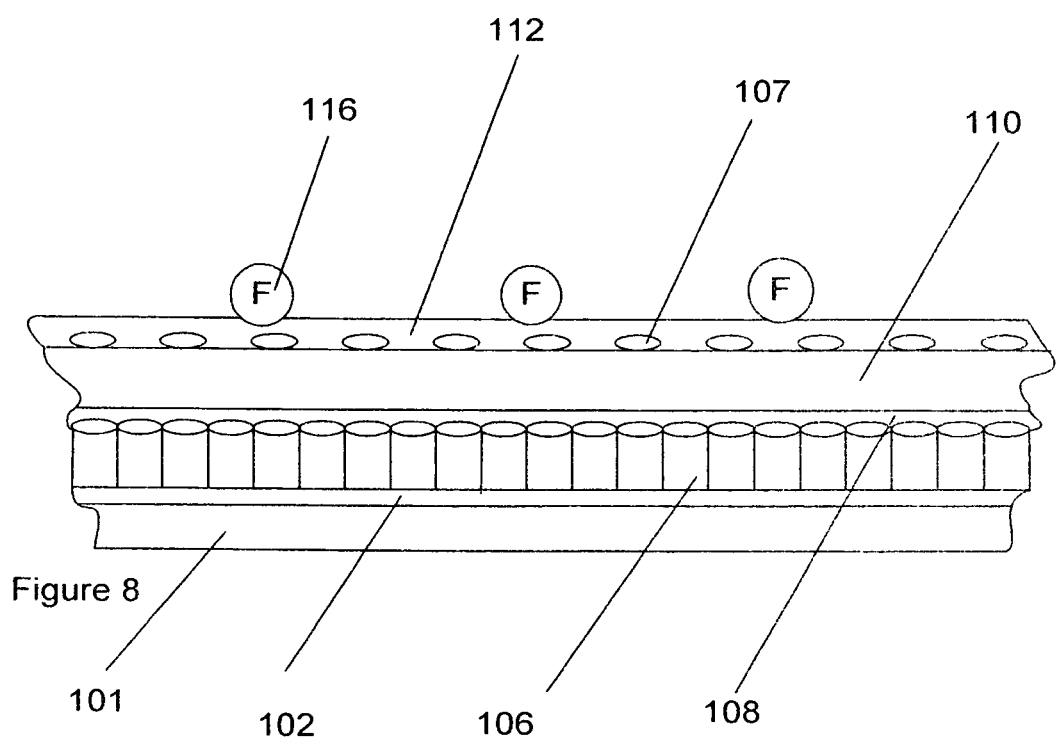
FIG. 8 is a diagrammatic depiction of a cross section of an embodiment of the invention involving two nanostructured metallic layers.

FIG. 8 is a diagrammatic depiction of a cross section of an embodiment of the invention involving two nanostructured metal layers. An even greater intensity effect is created if a secondary MEF layer is used, as shown in FIG. 8. Without regard to the specific planar substrate surface used, substrate 101, the MEF layers comprising the adhesion layer 102, optional alloy layer (not shown in FIG. 8), the a nanoparticle layer 106, the aqueous-impervious layer 108, and resonant spacer layer 110 are applied as described with reference to FIG. 1. On the top surface of the spacer layer 110 is deposited a second, relatively less optically dense nanoparticle layer 107. Over the top of this second layer is deposited a binding layer 112 which in turn acts according to the rules of the given assay to bind fluorescent labeled molecules 116 (also marked F) to the surface. Optionally, a second aqueous-impervious layer (not shown in FIG. 8) can be placed between the second nanoparticles layer 107 and the binding layer 112. This embodiment has enhanced sensitivity because the near proximity lifetime effects of MEF and the resonant intensity enhancement effects are combined yielding dramatic changes in lifetime and intensity relative to non-MEF surfaces.

It will be apparent to those skilled in the art that the examples and embodiments described herein are by way of illustration and not of limitation, and that other examples may be used without departing from the spirit and scope of the present invention, as set forth in the appended claims. Applicants have attempted to disclose all reasonably foreseeable equivalents. Unforeseeable insubstantial modifications may remain as equivalents.

I claim:

1. A structure for plasmon resonance augmentation of fluorescent emission from fluorescent molecules comprising:
   a substrate,
   a nanostructured film of silver, copper, titanium, aluminum, chromium, or tungsten metal or alloys thereof deposited on the top of the substrate,
   a spacer layer of optically transparent material deposited on top of the nanostructured film,
   the spacer layer comprised of aqueous impervious material capable of protecting the nanostructured film from degradation by aqueous media,
   the spacer layer having a physical thickness of about 50 to about 400 nanometers,
   wherein the plasmon resonance fluorescent emission augmentation is a function of the thickness of the spacer layer and the dielectric properties of the metal surface, and
   the plasmon resonance fluorescent emission augmentation is in the range of 20 fold or greater.

2. The structure of claim 1 wherein the metal or alloy film is between about 30 and about 300 nm thick.

3. The structure of claim 1 wherein the spacer layer is resonant at an optical wavelength.

4. The structure of claim 1 wherein the substrate is planar or three-dimensional.

5. The structure of claim 1 wherein the substrate is comprised of glass, silicon, or plastic.

6. The structure of claim 1 wherein the metal alloy consists of an aluminum alloy.

7. A structure for plasmon resonance augmentation of fluorescent emission from fluorescent molecules comprising:
   a substrate,
   a nanostructured film of aluminum-titanium metal alloy deposited on the top of the substrate,
   a spacer layer of optically transparent material deposited on top of the nanostructured film, wherein the nanostructured film comprises a more or less columnar metal structure with semi-hemispherical surface features having a mean surface diameter between about 20 and about 300 nm,
   the spacer layer comprised of aqueous impervious material capable of protecting the nanostructured film from degradation by aqueous media,
   the spacer layer having a physical thickness of about 50 to about 400 nanometers,
   wherein the plasmon resonance fluorescent emission augmentation is a function of the thickness of the spacer layer and the dielectric properties of the metal surface, and
   the plasmon resonance fluorescent emission augmentation is in the range of 20 fold or greater.

* * * * *